(12) United States Patent
Suzuki

(10) Patent No.: US 11,806,181 B2
(45) Date of Patent: Nov. 7, 2023

(54) DISPLAY SYSTEM, DISPLAY CONTROL DEVICE, AND DISPLAY CONTROL METHOD

(71) Applicant: Konica Minolta, Inc., Chiyoda-ku (JP)

(72) Inventor: Kenichirou Suzuki, Mitaka (JP)

(73) Assignee: KONICA MINOLTA, INC., Tokyo (JP)

( * ) Notice: Subject to any disclaimer, the term of this patent is extended or adjusted under 35 U.S.C. 154(b) by 329 days.

(21) Appl. No.: 16/828,295

(22) Filed: Mar. 24, 2020

(65) Prior Publication Data

US 2020/0305814 A1 Oct. 1, 2020

(30) Foreign Application Priority Data

Mar. 28, 2019 (JP) .................. 2019-062193

(51) Int. Cl.
| | |
|---|---|
| *G06F 3/0482* | (2013.01) |
| *G06F 16/26* | (2019.01) |
| *G06F 3/04817* | (2022.01) |
| *A61B 6/00* | (2006.01) |
| *A61B 5/00* | (2006.01) |
| *A61B 5/08* | (2006.01) |

(52) U.S. Cl.
CPC ............. *A61B 6/463* (2013.01); *A61B 5/08* (2013.01); *A61B 5/743* (2013.01); *A61B 5/7425* (2013.01); *A61B 5/7435* (2013.01); *A61B 5/7475* (2013.01); *A61B 6/465* (2013.01); *G06F 3/0482* (2013.01); *G06F 3/04817* (2013.01); *G06F 16/26* (2019.01)

(58) Field of Classification Search
None
See application file for complete search history.

(56) References Cited

U.S. PATENT DOCUMENTS

| | | | |
|---|---|---|---|
| 9,405,183 B2* | 8/2016 | Ando | G03B 42/02 |
| 11,250,048 B2* | 2/2022 | Kozuka | G06F 16/5838 |

(Continued)

FOREIGN PATENT DOCUMENTS

| | | |
|---|---|---|
| JP | 2005-040223 | 2/2005 |
| JP | 2005-270328 | 10/2005 |

(Continued)

OTHER PUBLICATIONS

Stange et al., "Dicomflex: A novel framework for efficient deployment of image analysis tools in radiological research," Sep. 11, 2018, PLoS One 13(9): e0202974, https://doi.org/10.1371/journal.pone.0202974.*

(Continued)

*Primary Examiner* — Ryan Barrett
(74) *Attorney, Agent, or Firm* — Cozen O'Connor

(57) ABSTRACT

A display system includes a hardware processor and a display that has a display screen and presents a display on the display screen on the basis of control exerted by the hardware processor. In a case of causing a thumbnail related to consecutive images sequentially acquired using X-rays at a plurality of different times to be displayed on the display screen, the hardware processor selects, as the thumbnail, an image in accordance with a setting previously determined for the consecutive images. An image other than a leading image of the consecutive images is included in the thumbnail.

11 Claims, 6 Drawing Sheets

(56) References Cited

U.S. PATENT DOCUMENTS

| | | | | |
|---|---|---|---|---|
| 2002/0033848 | A1* | 3/2002 | Sciammarella | G06F 3/0485 715/838 |
| 2002/0082484 | A1* | 6/2002 | Baba | A61B 6/00 600/300 |
| 2005/0259116 | A1* | 11/2005 | Araoka | G06T 19/00 345/619 |
| 2007/0174790 | A1* | 7/2007 | Jing | G06F 3/0485 715/838 |
| 2007/0242069 | A1* | 10/2007 | Matsue | G16H 30/40 345/428 |
| 2010/0246925 | A1* | 9/2010 | Nagatsuka | A61B 5/1135 382/132 |
| 2012/0036466 | A1* | 2/2012 | Venon | G06F 3/0482 715/810 |
| 2013/0091470 | A1* | 4/2013 | Sciammarella | G06F 3/0483 715/838 |
| 2014/0074759 | A1* | 3/2014 | Lewis | G06F 3/04817 706/12 |
| 2014/0219637 | A1* | 8/2014 | McIntosh | G11B 20/00007 386/282 |
| 2015/0310625 | A1* | 10/2015 | Shimamura | A61B 6/507 382/132 |
| 2015/0356271 | A1* | 12/2015 | Kozuka | A61B 6/563 705/2 |
| 2015/0370424 | A1* | 12/2015 | Joo | G06F 3/0485 715/830 |
| 2016/0212190 | A1* | 7/2016 | Kim | H04L 65/762 |
| 2016/0350923 | A1* | 12/2016 | Muraoka | G06T 7/0016 |
| 2016/0360116 | A1* | 12/2016 | Penha | G06F 3/04842 |
| 2017/0038951 | A1* | 2/2017 | Reicher | G06F 16/583 |
| 2017/0090739 | A1* | 3/2017 | Kozuka | G16H 30/20 |
| 2017/0091582 | A1* | 3/2017 | Takata | G06V 10/758 |
| 2017/0209716 | A1* | 7/2017 | Lugosi | G16H 30/20 |
| 2017/0213337 | A1* | 7/2017 | Lugosi | G06T 7/11 |
| 2017/0367623 | A1* | 12/2017 | Nakazawa | A61B 5/1128 |
| 2018/0335901 | A1* | 11/2018 | Manzari | G06F 3/0484 |
| 2018/0350130 | A1* | 12/2018 | Westerhoff | A61B 5/7475 |
| 2019/0096062 | A1* | 3/2019 | Westerhoff | A61B 6/5294 |
| 2020/0082531 | A1* | 3/2020 | de Vaan | G06T 7/337 |
| 2021/0390691 | A1* | 12/2021 | Matsutani | A61B 6/486 |
| 2022/0044395 | A1* | 2/2022 | Ebrahimi | G06F 16/58 |
| 2022/0139025 | A1* | 5/2022 | Westerhoff | G06T 11/001 345/424 |

FOREIGN PATENT DOCUMENTS

| | | |
|---|---|---|
| JP | 2006-314702 | 11/2006 |
| JP | 2009-036587 | 2/2009 |
| WO | WO 2017/061155 | 4/2017 |

OTHER PUBLICATIONS

Office Action dated Jul. 5, 2022 issued in Japanese Patent Application No. 2019-062193.

Office Action dated Apr. 26, 2022 issued in Japanese Patent Application No. 2019-062193.

\* cited by examiner

FIG. 4

EXAMINATION ID: 1234.567.890.12345

| SERIES ID | IMAGE TYPE | ANALYSIS SOURCE IMAGE | PROCESSING STATE | DATA |
|---|---|---|---|---|
| 1234.567.890.12345.1 | ORIGINAL_IMAGE | – | – | ○ |
| 1234.567.890.12345.2 | V_MODE_IMAGE | 1234.567.890.12345.1 | UNDER PROCESSING | ○ |
| 1234.567.890.12345.3 | P_MODE_IMAGE | 1234.567.890.12345.1 | COMPLETED | ○ |
| 1234.567.890.12345.4 | BS_IMAGE | 1234.567.890.12345.1 | COMPLETED | ○ |
| 1234.567.890.12345.5 | ENHANCED_IMAGE | 1234.567.890.12345.1 | COMPLETED | ○ |
| 1234.567.890.12345.6 | DIAPHRAGM_IMAGE | 1234.567.890.12345.1 | COMPLETED | ○ |

FIG. 5A

| PRESET NUMBER | CONDITION |
|---|---|
| 3 | IMAGES OF ALL OF ORIGINAL MODE, V MODE, P MODE, BS MODE, E MODE, AND D MODE EXIST |
| 2 | IMAGE OF ANY OF ABOVE MODES DOES NOT EXIST, AND IMAGE OF D MODE EXISTS |
| 1 | EXCEPT 2, 3 |

FIG. 5B

| PRESET NUMBER | DISPLAY ORDER | DISPLAY ID |
|---|---|---|
| 1 | ASCENDING ORDER OF SERIES_ID | 1 |
| 2 | ASCENDING ORDER OF SERIES_ID | 1 |
| 3 | ORIGINAL, GRAPH 1, GRAPH 2 | 1 |

FIG. 5C

| DISPLAY ID | IMAGE TYPE | THUMBNAIL IMAGE |
|---|---|---|
| 1 | ORIGINAL | LEADING |
| | V MODE | MAXIMUM EXPIRATION |
| | P MODE | MAXIMUM EXPIRATION |
| | D MODE | GRAPH |

DISPLAY SYSTEM, DISPLAY CONTROL DEVICE, AND DISPLAY CONTROL METHOD

BACKGROUND

1. Technological Field

The present invention relates to a display system, a display control device, and a display control method.

2. Description of the Related Art

Some computers can display captured medical images of a living body for a diagnostic purpose or the like. Images through use of X-rays are included in the medical images. In recent years, X-ray images have been subjected to not only an analysis and a diagnosis through use of a single still image, but also to a dynamics analysis of consecutively imaging and analyzing variations in an imaging target area, such as expansion and contract of lungs as well as movement of a blood vessel during respiration.

In consecutive image data such as a plurality of consecutive images and video, an image important for a diagnosis usually exists in the middle of the consecutive image data. Concerning this, JP2005-40223A discloses a technology of setting a mark at a desired image position in consecutive images to facilitate reading out a necessary image. A configuration in which small thumbnails associated with image data in the past are displayed in an array, and image data corresponding to a selected thumbnail is read out is used frequently.

SUMMARY OF THE INVENTION

However, in image data on consecutive images or video, a leading image is usually set as an image of a thumbnail. Therefore, there is a problem in that a thumbnail associated with necessary image data cannot be distinguished easily, and effort may be required until necessary image data is selected and made visible.

The present invention has an object to provide a display system, a display control device, and a display control method that enable a user to select desired image data more easily.

To achieve at least one of the abovementioned objects, according to an aspect of the present invention, a display system includes:
a hardware processor; and
a display that has a display screen and presents a display on the display screen on a basis of control exerted by the hardware processor, wherein
in a case of causing a thumbnail related to consecutive images sequentially acquired using X-rays at a plurality of different times to be displayed on the display screen, the hardware processor selects, as the thumbnail, an image in accordance with a setting previously determined for the consecutive images, and
an image other than a leading image of the consecutive images is included in the thumbnail.

According to another aspect of the present invention, a display control device includes:
a hardware processor, wherein
in a case of causing a thumbnail related to consecutive images sequentially acquired using X-rays at a plurality of different times to be displayed on a display screen of a display, the hardware processor selects, as the thumbnail, an image in accordance with a setting previously determined for the consecutive images, and
an image other than a leading image of the consecutive images is included in the thumbnail.

According to still another aspect of the present invention, a display control method for a display that has a display screen and presents a display on the display screen includes:
acquiring an external instruction; and
in a case of causing a thumbnail related to consecutive images sequentially acquired using X-rays at a plurality of different times to be displayed on the display screen, selecting, as the thumbnail, an image in accordance with a setting previously determined for the consecutive images, wherein
an image other than a leading image of the consecutive images is included in the thumbnail.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 4 is a chart describing image data being held.

FIG. 5A is a chart describing presets related to selection of a thumbnail.

FIG. 5B is a chart describing presets related to selection of a thumbnail.

FIG. 5C is a chart describing presets related to selection of a thumbnail.

FIG. 7A is a diagram showing another example of the list display screen.

FIG. 7B is a diagram showing another example of the list display screen.

DETAILED DESCRIPTION OF THE EMBODIMENTS

Hereinafter, one or more embodiments of the present invention will be described with reference to the drawings. However, the scope of the invention is not limited to the disclosed embodiments.

Figure 1:
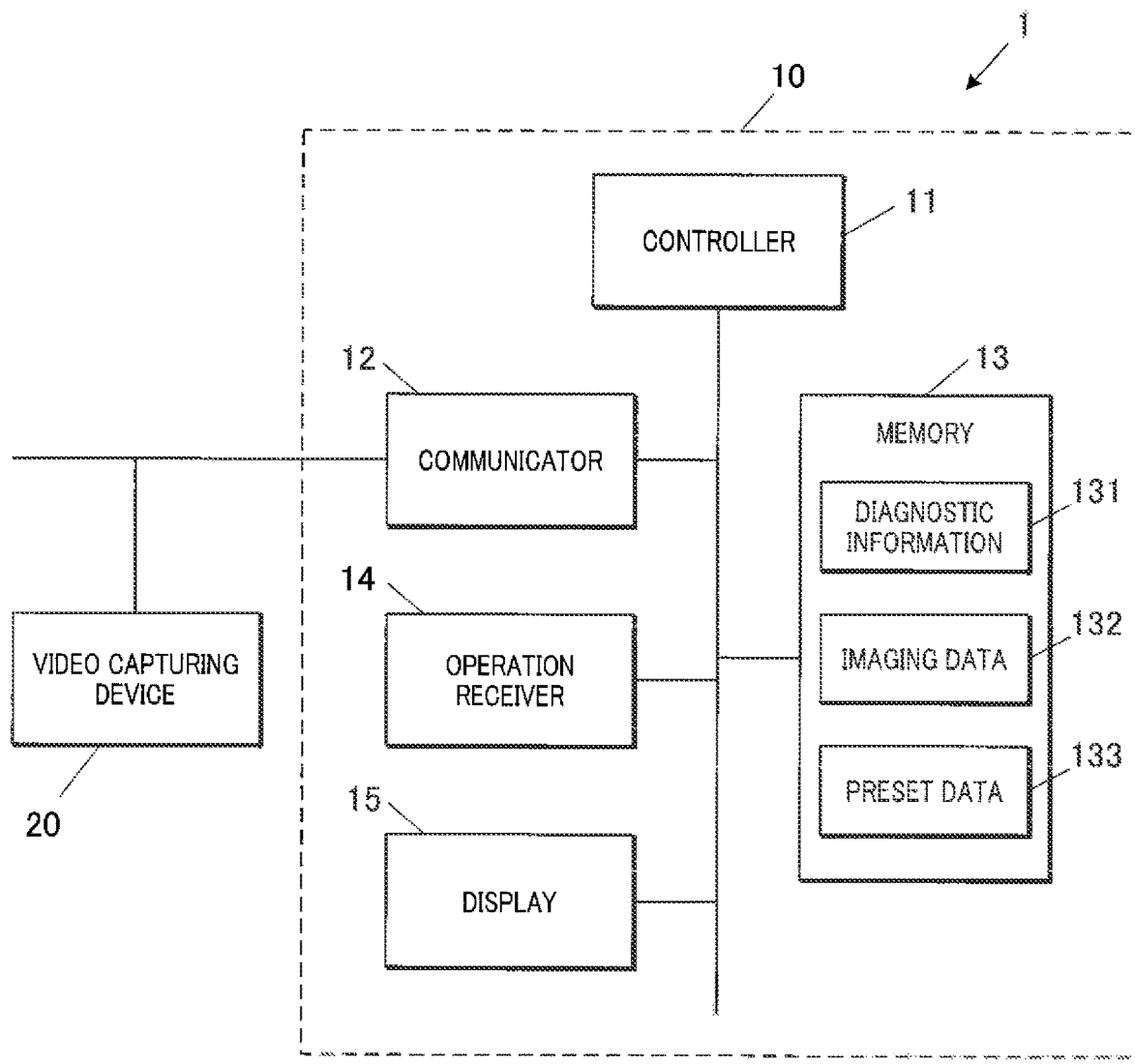
FIG. 1 is a block diagram showing a functional configuration of a display system.

FIG. 1 is a block diagram showing a functional configuration of a display system 1 including a computer 10 which is a display control device of the present embodiment.

The display system 1 includes the computer 10 and a video capturing device 20, which are connected via a network. The network may be wired connection via a local area network (LAN), or may be wireless connection through use of a wireless LAN or the like. A hub and/or router or the like may be included in the network, and data may be transmitted/received via them. The display system 1 may be part of a hospital information system and/or radiology information system.

The video capturing device 20 (also called a modality) consecutively acquires various images to be used for a medical diagnosis, herein, images (X-ray images) of lungs (chest) of a subject captured through use of X-rays. Data on X-ray images (consecutive images) captured (acquired) sequentially at a plurality of different times and arrayed may be a set of still image data or may be video data. An interval of capturing consecutive images as referred to herein may be wider than a frame interval of video defined generally as long as the interval is shorter than a time scale in accordance with changes in an imaging area, such as the respiratory cycle when imaging the lungs, for example, and the interval may not necessarily be always equal.

The video capturing device 20 has a controller not shown, and generates a header including identification information (imaging equipment, an imaging date and time, an imaging target, imaging conditions, and the like) described for acquired image data using tags on the basis of the standard of Digital Imaging and Communications in Medicine (DICOM), supplementary information, and the like. In the video capturing device 20, the controller can analyze captured X-ray image data to acquire differential data between temporally adjacent pieces of captured data, and can label an image acquired at a predetermined time among acquired images. In a lung image, cyclic expansion and contract occur in accordance with the respiration of a subject, so that a maximum expiration time at which the lungs contract most and a maximum inspiration time at which the lungs expand most are specified. For example, a temporally central time between the maximum expiration and maximum inspiration may be set as an intermediate time.

An image analysis device different from the video capturing device 20 may be provided separately so that image data output from the video capturing device 20 is analyzed and labeled in the image analysis device, rather than being analyzed and labeled in the video capturing device 20. The acquired and labeled image data is transmitted to the computer 10.

The computer 10 includes a controller 11 (hardware processor), a communicator 12, a memory 13, an operation receiver 14, a display 15, and the like. The computer 10 may be a typical personal computer (PC), or may be a processing device including a hardware configuration dedicated for processing of medical images.

The controller 11 includes a central processing unit (CPU), a random access memory (RAM), and the like, and is a processor that exerts integrated control over the operation of the computer 10. The controller 11 can read and execute a program stored in the memory 13 to enable selection and display of image data, input and display of comments on diagnostic details, and the like. The controller 11 can also subject input image data to analysis processing again.

The communicator 12 is connected to the above-described network to control communication between the computer 10 and the outside in conformity with a predetermined communication standard. Examples of the communication standard include Transmission Control Protocol/Internet Protocol (TCP/IP) related to the above-described LAN and the like, and the communicator 12 has a network card and the like adapted to them.

The memory 13 has a nonvolatile auxiliary storage device such as a hard disk drive (HDD) and/or a flash memory, and stores programs, setting data, imaging data, and the like. The memory 13 may have a memory such as a volatile memory (RAM) for temporarily storing large volume image data and/or its processed data, and the like.

For example, diagnostic information 131, imaging data 132, preset data 133 (previously determined settings), and the like are included in data to be stored in the memory 13. The diagnostic information 131 includes information related to a subject in image data having been captured and acquired. The diagnostic information 131 is associated with the imaging data 132 by means of the subject's ID or the like. The imaging data 132 includes image (X-ray image) data acquired from the video capturing device 20. The diagnostic information 131 and the imaging data 132 may each be stored in a memory of separate database devices or an identical database device, and read out according to necessity for temporal storage. The database device(s) or the computer 10 may be part of a picture archiving and communication system (PACS). The preset data 133 is setting data related to times in consecutive images suitable as thumbnails for the consecutive images as will be described later.

The operation receiver 14 receives an input operation externally performed by a user or the like for output to the controller 11 as an input signal. The operation receiver 14 receives an input operation such as a keyboard pressing operation, a pointing, clicking, or wheel rotating operation of a mouse, or the like, and/or a touch or drag on a touch panel, for example.

The display 15 has a digital display screen, such as, for example, a liquid crystal display screen (LCD), and performs a display operation on the digital display screen on the basis of the control exerted by the controller 11.

Next, types (image modes) of consecutive chest images targeted at the lungs will be described. In capturing of consecutive images, a usually captured image can be subjected to, in accordance with an area of interest, attenuation of a display of areas other than the area of interest or highlighting of the area of interest. For example, on the basis of a difference in variation properties in accordance with the respiration between the lungs and a tissue surrounding the lungs such as, for example, a bone, processing such as selectively weakening a display of the bone can be performed (BS mode (Bone Suppression)). To the contrary, processing of enhancing a display of a specific area in accordance with a difference in variation properties may be performed (E mode (Enhanced)).

The lungs expand and contract (dilate/constrict) in accordance with the state of respiration. At this time, the state of movement (the amount of movement and moving speed) of each of tissues of the lungs (specific positions such as, for example, apex portions of the lungs at the left and right upper ends and the diaphragm portion at the lower end) can be tracked (D mode (Diaphragm)). The amount of variations of a lung tissue from a predetermined state can also be calculated (V mode). Examples of the predetermined state include the state of maximum expiration and the like. It is also possible to calculate not only a lung tissue but also a difference of a lung vessel from a predetermined state, or the like (P mode). In this case, the predetermined state may be determined in conjunction with another measurement result such as the heart rate, besides the case of checking variations in a respiratory operation, such as the state of maximum inspiration.

Next, a display of captured images on the computer 10 of the present embodiment will be described.

Figure 2:
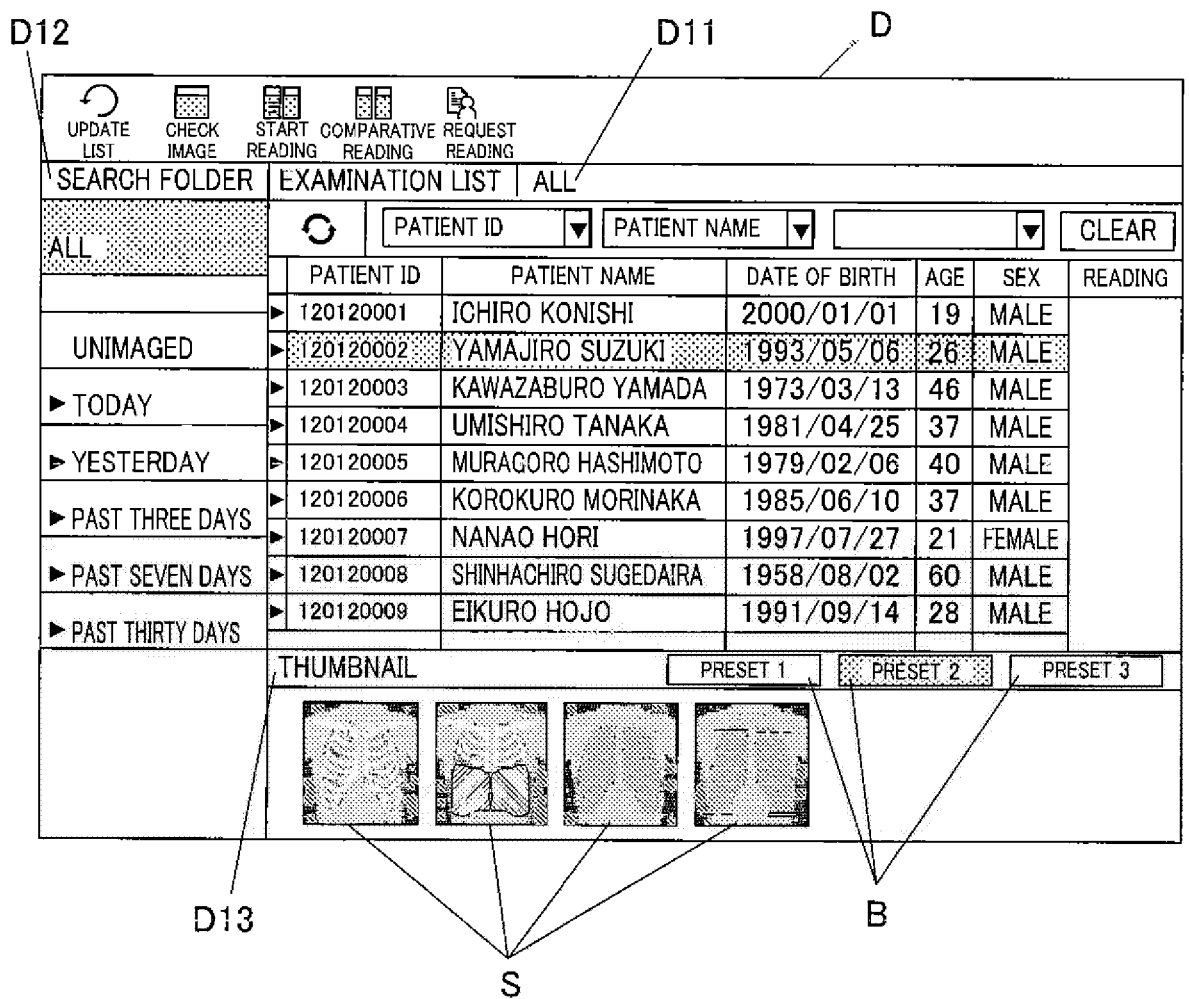
FIG. 2 is a diagram showing an example of a list display screen.

FIG. 2 is a diagram showing an example of a list display screen.

On a list display screen D, a list of all patients is displayed herein in an examination list window D11. In the examination list window D11, the patient ID, name, date of birth, age, sex, and the like are displayed. Herein, a patient having a patient ID "120120002" among them has been selected, and among captured images of this patient as a subject, thumbnails S of "all" of captured images set in a search folder window D12 are displayed in an array in a thumbnail window D13 on the lower side. The thumbnails S may have a resolution reduced from that of an original image. Image data of the thumbnails S having been set once may be stored and held in the memory 13.

Images other than the leading image of respective consecutive images may be included in this thumbnail S, and switching can be performed to display an image captured at any time. Since important times for a diagnosis have generally been determined for each image type (mode) (such as the state of maximum expiration, the state of maximum inspiration, or the intermediate state described above), these times are determined as a preset 1 to a preset 3, respectively, in the preset data 133. In these presets, an appropriate time may each be defined in accordance with the image type, or an identical time may be defined irrespective of the image type. When a preset selection button B associated with each of the preset 1 to the preset 3 is selected by a pointer operation performed by a user (an input operation received by the operation receiver 14, such as a mouse moving and clicking operation, is performed), an external instruction is acquired, and times determined by a preset setting in accordance with this external instruction are specified in the preset data 133, and the thumbnails S of images related to the times are selected and displayed. Since four thumbnails S are displayed herein, the four thumbnails S (all of which are displayed) are selected again on the basis of the preset data 133 when an external instruction related to a preset setting (herein, the preset 2) is acquired. This thumbnail S does not need to be a still image selected from among consecutive images, but may be video in which images at a plurality of times are connected sequentially and switched at predetermined time intervals, or the like.

Figure 3A:
FIG. 3A is a diagram showing another display example on the list display screen.
Figure 3B:
FIG. 3B is a diagram showing another display example on the list display screen.

FIG. 3A and FIG. 3B are diagrams showing other display examples on the list display screen.

As shown in FIG. 3A, a thumbnail may further be an analysis result of consecutive images, such as, for example, a graph display image, rather than any image among the consecutive images. Herein, a graph display image is included as a thumbnail Sa. A correspondence relation between graph contents and the type of captured consecutive images is usually well known to a user such as a physician, and the type of the consecutive images can be easily recognized by representing a graph display image by a thumbnail.

As shown in FIG. 3B, by arranging a pointer P on any thumbnail, it may be possible to display consecutive images M corresponding to a thumbnail Sb indicated with the pointer P in an enlarged manner.

FIG. 4 is a chart describing image data being held.

A processed image, analysis data, and the like provided with a series ID per series of contents related to a specific ID (examination ID: 1234.567.890.12345) related to an examination are held in the imaging data 132. Herein, for data on an original image having a series ID of "1234.567.890.12345.1", a series ID with the number at the end being incremented one by one is allocated to data on an image of each of the V mode, P mode, BS mode, E mode, and D mode obtained by processing the data on the original image. Herein, for example, data of the V mode is currently under processing (which may be reprocessing), and data of the other modes has already been processed.

FIG. 5A to FIG. 5C are charts describing presets related to selection of a thumbnail.

A preset is explicitly designated selectively by a user (manually designated) in some cases, and is automatically designated in accordance with the data type of images being held in other cases. In this designation method, a user-determined instruction (an external instruction) can be input separately on a setting screen or the like. Alternatively, a preset may be automatically designated at the initial start-up, and then the user may be allowed to manually input an instruction to designate a switch to any other preset. A chart showing designation conditions in the case where a preset is automatically designated is shown in FIG. 5A. In a case where, in addition to an original image, images of all of the V mode, P mode, BS mode, E mode, and D mode for the original image are held, a preset number "3" is selected. In a case where an image of at least any of the above-described six modes excluding the D mode does not exist, a preset number "2" is selected. In a case where neither the preset number "2" nor "3" is selected, that is, in a case where an image of the D mode does not exist, a preset number "1" is selected.

FIG. 5B is a chart showing a display order of thumbnails of respective images in accordance with the preset number and a selection criterion of images to be used as thumbnails. In the case where the preset number is "1" or "2", the display order of thumbnails is determined by the series ID ("SERIES_ID"), for example. On the other hand, in the case where the preset number is "3", an original image, a graph 1, and a graph 2 are displayed in this order in a fixed manner. Herein, for example, the graph 1 is an analysis image in the D mode, and the graph 2 is an analysis image in the P mode. In each of these presets, images of thumbnails to be selected are determined as described above. That is, a time appropriate as a thumbnail is held previously as the preset data 133, and can be selectively switched in accordance with a user's intention or the like.

The display ID indicates an image selected as a thumbnail for the type of respective consecutive images. As shown in FIG. 5C, the leading image is selected as an image of a thumbnail as usual for original consecutive images. In contrast, in the V mode and P mode, an image at a time indicating the state of maximum expiration is selected as a thumbnail. For an image of the D mode, a graph (the graph 1) obtained on the basis of a captured image by the D mode is set as a thumbnail.

Contents of the charts shown in FIG. 5B and FIG. 5C do not depend upon whether the preset is designated manually or automatically. That is, for the number of a manually designated preset, the display order of respective images is determined and an image to be displayed as a thumbnail is selected on the basis of FIG. 5B and FIG. 5C.

Figure 6:
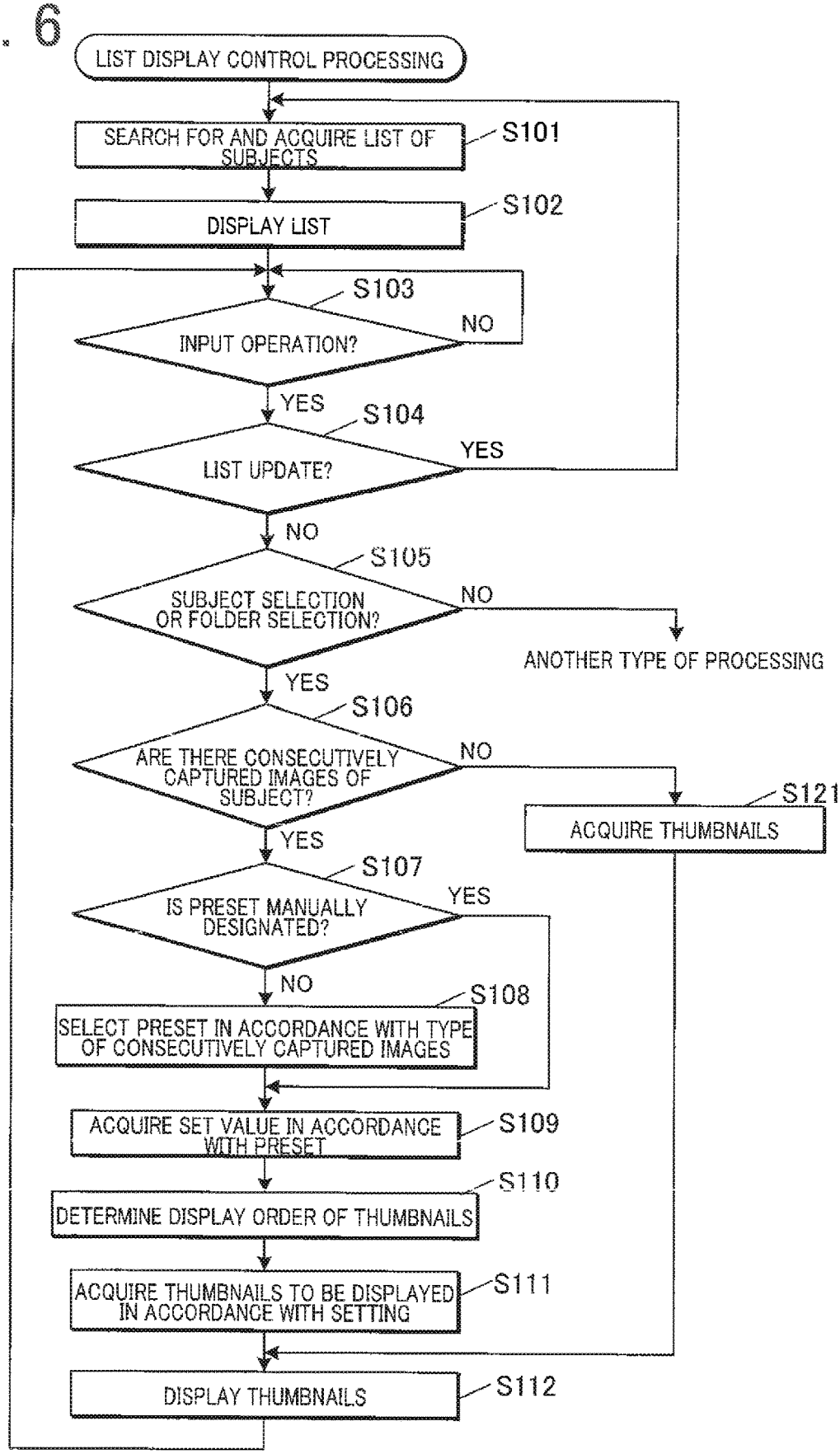
FIG. 6 is a flowchart showing a control procedure of list display control processing.

FIG. 6 is a flowchart showing a control procedure performed by the controller 11 in list display control processing executed by the computer 10. This processing including display control processing of the present embodiment is initiated in a case where a list display instruction for medical diagnostic images (herein, X-ray images) of a patient (subject) is invoked. This processing may be a sub-process invoked from another type of processing.

When the list display control processing is started, the controller 11 searches for a list of patients (subjects), and acquires list data on the patients (subjects) (step S101). The controller 11 outputs an instruction to cause the acquired patients to be displayed in a list on the display screen to the display 15 (step S102).

The controller 11 determines whether an input operation has been received by the operation receiver 14 (step S103). In a case where it is determined that an input operation has not been received ("NO" in step S103), the controller 11 repeats the processing of step S103. In a case where it is determined that an input operation has been received ("YES" in step S103), the controller 11 determines whether an operation detail is a list update instruction (step S104). In a case where it is determined that an operation detail is a list update instruction ("YES" in step S104), the processing of the controller 11 returns to step S101.

In a case where it is determined that an operation detail is not a list update instruction ("NO" in step S104), the controller 11 determines whether the input operation is an operation of selecting a subject (patient) or an instruction to select a search folder related to examination images of the selected subject (step S105). In a case where it is determined that neither applies ("NO" in step S105), the controller 11 executes another type of processing (including an instruction to terminate the list display control processing) in accordance with the detail of the input operation.

In a case where it is determined that the input operation is an operation of selecting a subject from a display list or an instruction to select a search folder related to examination images of the subject ("YES" in step S105), the controller 11 extracts images relevant to a selected folder among examination images of the subject, and determines whether consecutively captured images (dynamics analysis images) are included in the extracted images (step S106). In a case where it is determined that consecutively captured images are not included ("NO" in step S106), the controller 11 acquires thumbnails of respective still images, and sorts the thumbnails by "SERIES_ID" or the like to determine the display order (step S121). The processing of the controller 11 then transitions to step S112.

In a case where it is determined that consecutively captured images are included ("YES" in step S106), the controller 11 determines whether a preset is to be manually designated (step S107). In a case where it is determined that a preset is not to be manually designated (a preset is to be automatically designated) ("NO" in step S107), the controller 11 selects a preset in accordance with the type of the consecutively captured images having been extracted (step S108). The processing of the controller 11 then transitions to step S109. In a case where it is determined that a preset is to be manually designated ("YES" in step S107), the processing of the controller 11 transitions to step S109.

Upon transitioning to processing of step S109, the controller 11 acquires a setting of a thumbnail in accordance with the value of the preset having been set (step S109; an acquisition step). The controller 11 determines consecutively captured images for which thumbnails are to be displayed and the order of displaying them on the basis of the setting (step S110). The controller 11 selects and acquires thumbnails related to the consecutively captured images targeted for display (step S111; a selection step). The processing of the controller 11 then transitions to step S112.

Upon transitioning to processing of step S112, the controller 11 outputs an instruction to cause the acquired images to be displayed by thumbnails in the display order having been set to the display 15 (step S112). The processing of the controller 11 then returns to step S103.

Figures 7A, 7B:
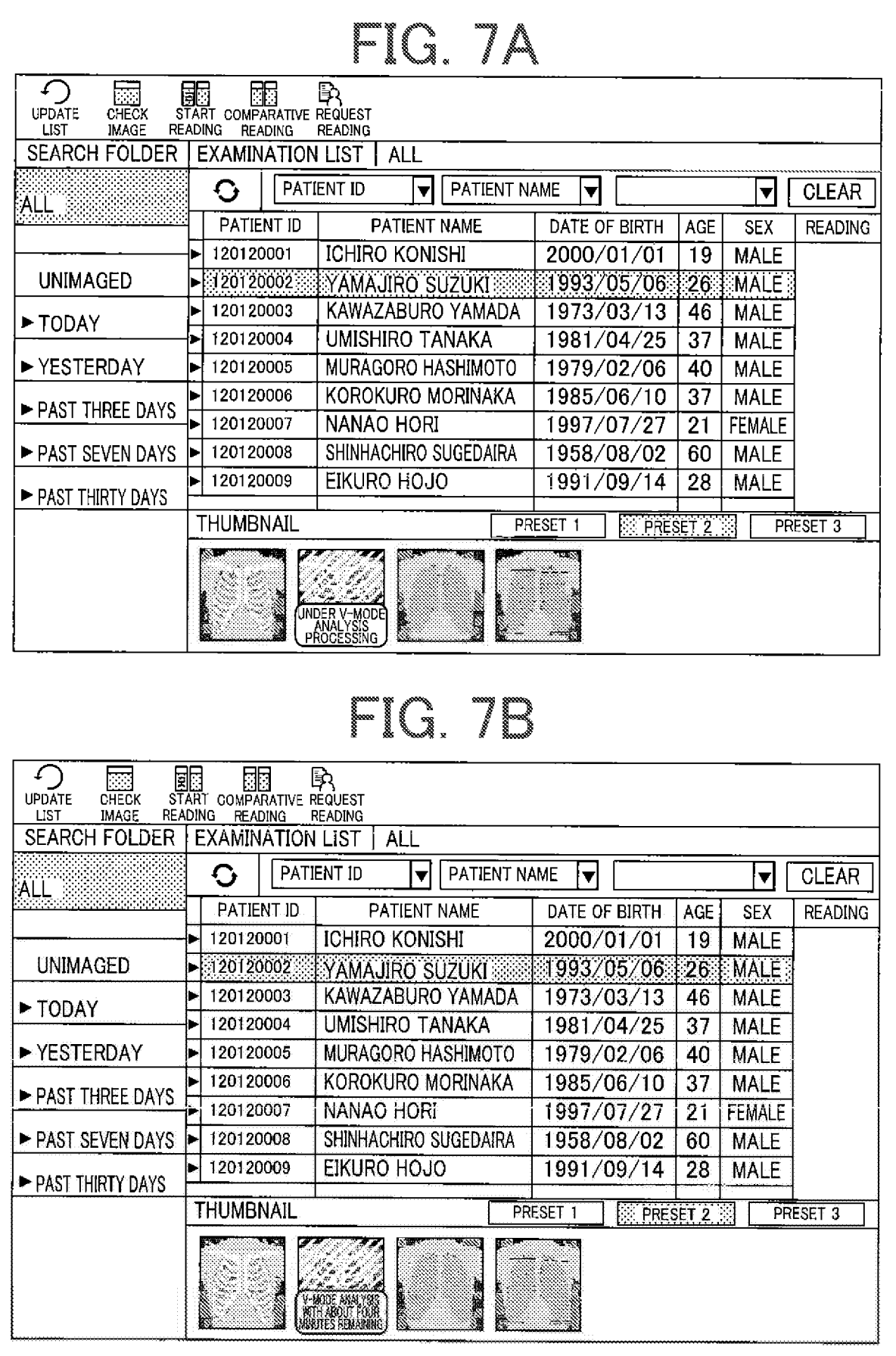

FIG. 7A and FIG. 7B are diagrams showing other examples of the list display screen.

In the computer 10, the controller 11 can analyze image data again as described above. In such a case where an image analysis device is provided separately, and image data is stored in another database device, re-analysis processing may be performed in parallel to list display. These types of processing are often caused to be performed by a user's manual instruction. In such a case, the fact that image processing is being performed may be displayed on a thumbnail as shown in FIG. 7A. Further, an expected time until the image processing is terminated may be displayed as shown in FIG. 7B. By superimposing such a display on a thumbnail in a list display, the user can be easily informed of a progress status of processing during the processing while advancing another type of processing. A diagnosis based on the image data, or the like can be started immediately after the processing is terminated.

As described above, the display system 1 including the computer 10 of the present embodiment includes the controller 11 and the display 15 that has a display screen and presents a display on the display screen on the basis of control exerted by the controller 11. In a case of causing a thumbnail related to consecutive images sequentially acquired using X-rays at a plurality of different times to be displayed on the display screen, the controller 11 selects, as the thumbnail, an image in accordance with a setting previously determined for the consecutive images, and images other than the leading image of the consecutive images are included in the thumbnail.

In this manner, by extracting an image appropriately indicating the display contents from consecutive images for use as a thumbnail, the user can more easily select desired image data to be displayed. Such a thumbnail setting is previously set and held as the preset data 133, and a necessary setting is selected in the display system 1 in accordance with an input instruction related to automatic designation, manual designation, or the like. Thus, a switching setting can be made appropriately in accordance with diagnostic details, an image type, or the like.

A graph display image related to an analysis result of consecutive images is included in an image to be selected as a thumbnail. Since a correspondence relation between the type of consecutive images and an analysis graph is well known to those who perform image-based diagnoses, it is also possible to cause a user to efficiently determine a desired image by causing an image of an analysis graph to be displayed as a small thumbnail.

A plurality of thumbnails can be displayed in an array on the display screen, and in a case where a predetermined external instruction is acquired, the controller 11 re-selects all the thumbnails to be displayed on the display 15 in accordance with a setting. That is, once a preset is selected, thumbnails of various types of image data are set again collectively, and displayed in a converted manner. Thus, effort can be reduced further to enable necessary image data to be efficiently selected from among the thumbnails.

The display system 1 also includes the operation receiver 14 that receives an input operation, and the controller 11 acquires an external instruction on the basis of the input operation received by the operation receiver 14. That is, since a preset is easily selected by operating the mouse or the like, a thumbnail of a necessary image can be efficiently displayed without taking effort.

The preset is determined in accordance with the type of consecutive images. Since times at which characteristic images are captured have generally been settled in various consecutive images, a thumbnail can be efficiently switched to a necessary image without increasing alternatives more than necessity by determining the preset in accordance with the type.

The controller 11 selects images captured at a plurality of times from among consecutive images on the basis of the preset, and sets video obtained by sequentially connecting the images captured at the plurality of times as a thumbnail. That is, the thumbnail does not need to be a still image. Since changes in each portion in consecutive images draw attention in a dynamics analysis, the user can specify a desired image more efficiently by extracting some of a plurality of images to be displayed sequentially so as to indicate what changes are drawing attention.

The consecutive images are captured images of the chest (lungs) of a subject, and an image at a time of at least any of the state of maximum expiration, the state of maximum inspiration, and a predetermined intermediate state between the state of maximum expiration and the state of maximum inspiration during respiration is included in images selected on the basis of the preset.

In a dynamics analysis through use of chest images, situations such as movement and deformation of the lungs and their peripheral specific areas in accordance with respiration are important in many cases, and in particular, a difference is likely to significantly occur in a state where air is inhaled most and a state where air is exhaled most. Therefore, by including these states in the preset, it is easy for the user to determine whether the thumbnail is a desired image more easily and reliably.

In a case where a thumbnail is indicated with a pointer in the display screen in accordance with an input operation, the controller 11 causes consecutive images related to the thumbnail to be displayed. In addition to appropriately determining a display of a thumbnail as described above, by further locating the pointer (arrow display) on the thumbnail by a mouse operation or the like to cause consecutive images corresponding to the thumbnail to be displayed in an enlarged manner, it is possible to check in advance whether an image to be selected by means of the thumbnail is correct even without actually making a selection. Thus, an error in the selection operation can be reduced further to reduce effort.

The display system 1 also includes the memory 13 that stores a selected thumbnail. By holding a once generated thumbnail, effort of generating a thumbnail each time can be eliminated, and burdens on the controller 11 can be reduced. A time lag until a thumbnail is displayed when causing list display to be performed can also be controlled.

Since an image appropriately indicating display contents can be extracted from consecutive images for use as a thumbnail using the computer 10 including the above-described controller 11, the user can select desired image data, in particular, consecutive image data more easily. Such a thumbnail setting is previously set and held as the preset data 133, and the controller 11 selects a necessary setting in accordance with an input instruction. Thus, a switching setting can be made appropriately in accordance with diagnostic details, an image type, or the like.

By using the above-described display control method related to a thumbnail display setting, a thumbnail can be switched and set to an image at an appropriate time in the middle of consecutive images which is preferable for the user or the like in accordance with the preset data 133 previously set and held. Thus, the user can select desired image data more easily.

The present invention is not limited to the above-described embodiment, but can be modified variously. For example, a terminal device different from the computer 10 may have the operation receiver 14 and the display 15. In this case, the computer 10 may receive an input signal from the operation receiver 14 (the terminal device) via the communicator 12, and may transmit an output signal to the display 15 (the terminal device).

Although a description has been made in the above-described embodiment that the presets 1 to 3 are fixed, contents of the presets themselves may be changed. It may be possible to perform customization such that only a selection button for a preset necessary for the user among a larger number of presets is displayed on the display screen.

Although a description has been made in the above-described embodiment using a preset in accordance with the type of consecutive images and a preset that causes a graph display image of an analysis result to be displayed as examples, they may be mixed. A thumbnail has been described using a single selected still image or video obtained by connecting a plurality of images as an example, but may be a single composite image produced by superimposing a plurality of images.

Although a description has been made in the above-described embodiment that all the thumbnails are converted collectively in accordance with a preset, it may be possible to convert only an image indicated with the pointer in accordance with the preset. In this case, a selection menu may be temporarily invoked without using the preset selection button B to enable designation of a preset.

Although a description has been made in the above-described embodiment that the operation receiver 14 receives an external instruction, information related to an external instruction may be acquired via the communicator 12.

Although a description has been made in the above-described embodiment using captured images of the chest (lungs) as an example, the present invention may be used for displaying images related to a radiographic dynamics analysis for another area.

In addition, specific details such as the specific configuration, display contents, and display control procedure presented in the above-described embodiment may be modified appropriately within the scope of the present invention.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese patent application No. 2019-062193, filed on Mar. 28, 2019, is incorporated herein by reference in its entirety.

What is claimed is:
1. A display system comprising:
a hardware processor;
a video capturing device; and
a display that has a display screen and presents a display on the display screen on a basis of control exerted by the hardware processor, wherein the hardware processor is configured to:
generate a header including identification information and supplementary information described for acquired image data using tags on the basis of a standard of Digital Imaging and Communications in Medicine (DICOM);
analyze the image data to select, an image as a thumbnail, in accordance with a setting determined for a type of dynamics analysis images acquired by consecutively X-ray imaging and analyzing variations in an imaging target area; and display the thumbnail related to the dynamics analysis images on the display screen, wherein, an image other than a leading image of the dynamics analysis images is included in the thumbnail,
wherein the hardware processor defines a plurality of settings in accordance with each combination of types of a plurality of images including at least an original image of the dynamics analysis image and a processed image obtained by processing the original image, and
the hardware processor causes the thumbnail of the original image and the processed image corresponding to the setting to be displayed on the display screen.

2. The display system according to claim 1, wherein a graph display image related to an analysis result of the dynamics analysis images is included in the image selected as the thumbnail.

3. The display system according to claim 1, wherein
a plurality of the thumbnails can be displayed on the display screen, and
in a case where a predetermined external instruction is acquired, the hardware processor re-selects all of the thumbnails to be displayed on the display in accordance with the setting.

4. The display system according to claim 3, comprising:
an operation receiver that receives an input operation, wherein
the hardware processor acquires the external instruction on a basis of an input operation received by the operation receiver.

5. The display system according to claim 1, wherein
the hardware processor selects images acquired at a plurality of times from among the dynamics analysis images in accordance with the setting, and sets video obtained by sequentially connecting the images acquired at the plurality of times as the thumbnail.

6. The display system according to claim 1, wherein
the dynamics analysis images are captured images of the chest of a subject, and
the image selected on a basis of the setting includes an image acquired at a time of at least any of a state of maximum expiration, a state of maximum inspiration, and a predetermined intermediate state between the state of maximum expiration and the state of maximum inspiration during respiration.

7. The display system according to claim 1, comprising:
an operation receiver that receives an input operation, wherein
in a case where the thumbnail is indicated with a pointer in the display screen in accordance with the input operation, the hardware processor causes the dynamics analysis images related to the thumbnail to be displayed.

8. The display system according to claim 1, comprising:
a memory that stores the thumbnail having been selected.

9. The display system according to claim 1, wherein the hardware processor causes a plurality of selection buttons associated with the respective plurality of the settings to be displayed on the display screen, and
the hardware processor determines the setting associated with the selection button, in response to selection of one of the selection buttons according to an input operation received by an operation receiver.

10. A display control device, comprising:
a hardware processor, wherein the processor is configured to:
generate a header including identification information and supplementary information described for acquired image data using tags on the basis of a standard of Digital Imaging and Communications in Medicine (DICOM);
select, from dynamics analysis images acquired by consecutively X-ray imaging and analyzing variations in an imaging target area, a thumbnail, and analyze the image data to select, an image as a thumbnail, in accordance with a setting determined for a type of dynamics analysis images acquired by consecutively X-ray imaging and analyzing variations in an imaging target area; and
display the thumbnail related to the dynamics analysis images on a display screen, wherein, an image other than a leading image of the dynamics analysis images is included in the thumbnail;
define a plurality of the settings in accordance with each combination of types of a plurality of images including at least an original image of the dynamics analysis image and a processed image obtained by processing the original image; and
display on the display screen the thumbnail of the original image and the processed image corresponding to the setting.

11. A display control method for a display that has a display screen and presents a display on the display screen under control of a hardware processor, comprising:
generating a header including identification information and supplementary information described for acquired image data using tags on the basis of a standard of Digital Imaging and Communications in Medicine (DICOM);
analyzing the image data to select, by the hardware processor, an image as a thumbnail, in accordance with a setting determined for a type of dynamics analysis images acquired by consecutively X-ray imaging and analyzing variations in an imaging target area;
displaying, by the hardware processor, the thumbnail related to the dynamics analysis images on the display screen, wherein an image other than a leading image of the dynamics analysis images is included in the thumbnail;
defining a plurality of the settings in accordance with each combination of types of a plurality of images including at least an original image of the dynamics analysis image and a processed image obtained by processing the original image; and
displaying on the display screen the thumbnail of the original image and the processed image corresponding to the setting.

* * * * *